United States Patent [19]

Thome et al.

[11] Patent Number: 5,349,097
[45] Date of Patent: Sep. 20, 1994

[54] CATALYTIC ISOMERIZATION OF α-ALKENOLS

[75] Inventors: Alfred Thome, Ludwigshafen; Michael Roeper, Wachenheim; Heinz-Josef Kneuper, Mannheim, all of Fed. Rep. of Germany

[73] Assignee: BASF Aktiengesellschaft, Ludwigshafen, Fed. Rep. of Germany

[21] Appl. No.: 99,236

[22] Filed: Jul. 29, 1993

[30] Foreign Application Priority Data

Aug. 29, 1992 [DE] Fed. Rep. of Germany ....... 4228887

[51] Int. Cl.$^5$ ...................... C07C 29/56; C07C 33/02; C07C 35/17
[52] U.S. Cl. .................... 568/906; 568/828; 568/838; 568/843; 568/849; 568/875
[58] Field of Search ............... 568/906, 875, 828, 838, 568/843, 849

[56] References Cited

U.S. PATENT DOCUMENTS

| | | | |
|---|---|---|---|
| 2,801,266 | 7/1957 | Schinz | 568/906 |
| 3,355,505 | 11/1967 | Tedeschi | 568/906 |
| 3,696,155 | 10/1972 | Mueller et al. | 568/906 |
| 3,925,485 | 12/1975 | Chabardes et al. | 568/824 |
| 3,997,577 | 12/1976 | von Fraunberg | 568/875 |
| 4,006,193 | 2/1977 | Ninagawa et al. | 568/906 |
| 4,087,472 | 5/1978 | Hughes | 568/906 |
| 4,254,291 | 3/1981 | Kane | 568/875 |
| 4,645,863 | 2/1987 | Rebafka et al. | 568/899 |
| 4,962,243 | 10/1990 | Roeper et al. | 568/909.5 |

FOREIGN PATENT DOCUMENTS

| | | | |
|---|---|---|---|
| 0373488 | 4/1991 | European Pat. Off. . | |
| 3902357 | 8/1990 | Fed. Rep. of Germany . | |
| 17406 | 2/1977 | Japan | 568/906 |
| 139027 | 8/1982 | Japan | 568/906 |

OTHER PUBLICATIONS

J. Am. Chem. Soc. 61, 2564 (1939).
Angew. Chem. 100, 420 (1988).
Angew. Chem. 103, 183 (1991).
J. Organomet. Chem 297, C5 (1985).
Angew. Chem. 100, 1269 (1988).
J. Organomet. Chem. 382, 1 (1990).

Primary Examiner—Joseph E. Evans
Attorney, Agent, or Firm—John H. Shurtleff

[57] ABSTRACT

A process for the catalytic isomerization of secondary α-alkenols of formula I

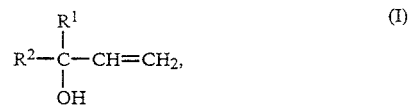

in which $R^1$ is a $C_1-C_{20}$ alkyl group or a $C_2-C_2$ alkenyl group and in which $R^2$ stands for hydrogen, a halogen atom, a $C_1-C_{10}$ alkoxy group, a carbonyl group, or a $C_1-C_{20}$ alkyl group and in which $R^1$ and $R^2$ can be joined together to complete a five-membered or six-membered carbocyclic ring, to primary α-alkenols of formula II

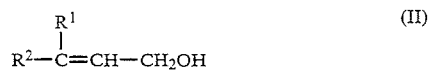

or for the isomerization of primary α-alkenols of formula II to secondary α-alkenols of formula I, wherein the isomerization is carried out in the presence of organotrioxorhenium(VII) compounds of formula III

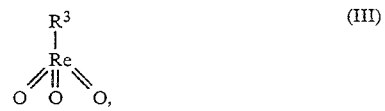

in which $R^3$ is a $C_1-C_{10}$ alkyl group, a cyclopentadienyl group substituted by from one to five $C_1-C_4$ alkyl groups, an unsubstituted cyclopentadienyl group, a $C_6-C_{10}$ aryl group, or a $C_7-C_{11}$ aralkyl group, or wherein the isomerization is carried out in the presence of organotrioxorhenium(VII) compounds of formula III attached to a polymeric support.

11 Claims, No Drawings

CATALYTIC ISOMERIZATION OF α-ALKENOLS

The present invention relates to a process for the catalytic isomerization of secondary α-alkenols of formula I

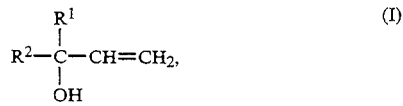

in which $R^1$ is a $C_1$-$C_{20}$ alkyl group or a $C_2$-$C_{20}$ alkenyl group and in which $R^2$ stands for hydrogen, a halogen atom, a $C_1$-$C_{10}$ alkoxy group, a carbonyl group or a $C_1$-$C_{20}$ alkyl group, and in which $R^1$ and $R^2$ can be joined together to complete a five-membered or six-membered carbocyclic ring, to primary α-alkenols of formula II

or for the isomerization of primary α-alkenols of formula II to secondary α-alkenols of formula I.

The isomerization of the allyl alcohols I to the corresponding allyl alcohols II and vice versa is an equilibrium reaction. It can be catalyzed by different types of catalysts, e.g., Broenstedt-acids (cf *J. Am. Chem. Soc.* 61, 2564 (1939)) or transition metal compounds. Since isomerization by means of Broenstedt-acids can lead to a large number of undesirable side reactions depending on the substrate, attempts were made at an early stage to find transition metal compounds which catalyze this reaction with greater selectivity.

DE-A 2,752,986 describes the isomerization of allyl alcohols with the aid of palladium complexes. On account of their high price and the fact that palladium complexes are chemically not very stable and that under the conditions used for the reaction and subsequent purification they show a tendency to form deposits of finely divided metallic palladium on the inner surfaces of the reaction equipment, this method is unsuitable for industrial purposes.

In U.S. Pat. No. 4,006,193 there are used a series of compounds of Group Vb, Group VIb, and Group VIIb transition metals in the periodic table for the isomerization of allyl alcohols. Although this reference names a number of transition metal compounds as being suitable catalysts for this isomerization, vanadium compounds are in fact preferably used as isomeration catalysts, in particular salts of vanadic acid and esters thereof with aliphatic alcohols, since these compounds yield the best results with respect to yield and selectivity. Rhenium compounds, in particular the esters, anhydrides, and ammonium salts of perrhenic acid, are also referred to in this reference as being suitable catalysts, but the only example of isomerization by means of a rhenium compound, i.e. ammonium perrhenate, shows a distinctly worse yield and a distinctly poorer selectivity than the analogous reaction with vanadium compounds.

U.S. Pat. No. 3,925,485 also states that the best results in the isomerization of primary and secondary allyl alcohols are achieved with vanadium compounds. This reference also gives a number of rhenium compounds as being suitable isomerization catalysts. However, no examples illustrating the isomerization of allyl alcohols by means of one of these rhenium compounds are given in this reference.

Although, according to U.S. Pat. Nos. 4,006,193 and 3,925,485, the best results in the isomerization of allyl alcohols are achieved using catalysts containing vanadium compounds, as compared with catalysts containing compounds of the other transition metals in Groups Vb, VIb, and VIIb in the periodic table, the use of vanadium compounds again leads only to unsatisfactory results with regard to the selectivity of the isomerization reaction, so that the use of the processes of these two patents for the mass-production of chemicals, e.g., precursors for plasticizing alcohols, is uneconomical, even in their most preferred embodiments, as a result of the high occurrence of unusable by-products.

In the telomerization of butadiene with water (cf. e.g., U.S. Pat. No. 4,962,243) according to equation (1)

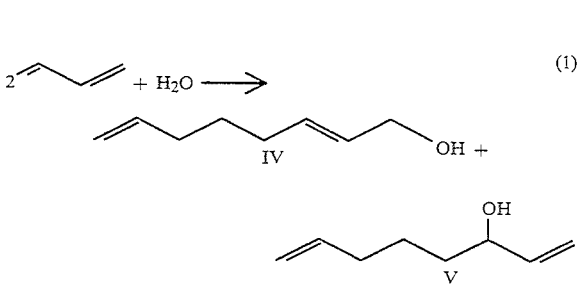

and when adding water to butadiene (cf, e.g., U.S. Pat. No. 4,645,863) according to equation (2)

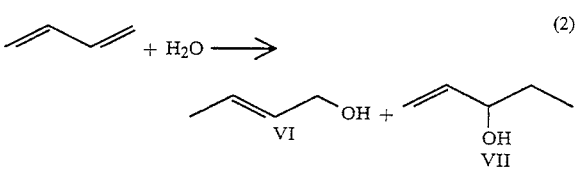

the undesirable secondary octadienol V or the undesirable secondary butenol VII is formed to a considerable degree as by-product. Since, however, only the primary alkenols IV and VI can be hydrogenated to alkanols, n-octanol, or n-butanol, which serve as plasticizer alcohols or solvents, a process for the isomerization of allyl alcohols is required which is capable of being carried out on an industrial scale at high conversion rates and showing good selectivity.

It is thus an object of the present invention to find a process for the isomerization of primary or secondary allyl alcohols, which makes said isomerization possible and gives high yields and selectivity and thus makes the use of this reaction possible and economical for large-scale operations, in particular, for example for the isomerization of the secondary octadienol V. In particular, it is desirable to find more effective and more selective catalysts than those known in the art and suitable working-up methods which lead to reduced formation of undesirable by-products.

Accordingly, we have found a process for the catalytic isomerization of secondary α-alkenols of formula I

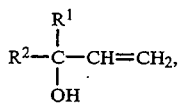

(I)

in which $R^1$ is a $C_1$–$C_{20}$ alkyl group or a $C_2$–$C_{20}$ alkenyl group and in which $R^2$ stands for hydrogen, a halogen atom, a $C_1$–$C_{10}$ alkoxy group, a carbonyl group, or a $C_1$–$C_{20}$ alkyl group and in which $R^1$ and $R^2$ can be joined together to complete a five-membered or six-membered carbocyclic ring, to primary α-alkenols of formula II

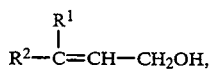

(II)

or for the isomerization of primary α-alkenols of formula II to secondary α-alkenols of formula I, wherein the isomerization is carried out in the presence of organotrioxorhenium(VII) compounds of formula III

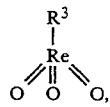

(III)

in which $R^3$ is a $C_1$–$C_{10}$ alkyl group, a cyclopentadienyl group substituted by from one to five $C_1$–$C_4$ alkyl groups, an unsubstituted cyclopentadienyl group, a $C_6$–$C_{10}$ aryl group, or a $C_7$–$C_{11}$ aralkyl group, or wherein the isomerization is carried out in the presence of organotrioxorhenium(VII) compounds of formula III attached to a polymeric support.

The isomerization catalysts III to be used in the present invention comprise a relatively new class of rhenium compounds, the production of the first representatives of which began in the mid-eighties. Methyltrioxorhenium(VII) ($R_3 = CH_3$), for example, was obtained for the first time in 1988 by treatment of dirhenium heptoxide ($Re_2O_7$) with tetramethyltin (*Angew. Chem.* 100, 420 (1988)). Higher alkyl- and aryl-trioxorhenium(VII) compounds have been only recently obtainable by the reaction of dirhenium heptoxide with dialkylzinc compounds as described in *Angew. Chem.* 103, 183 (1991) and cyclopentadienyltrioxorhenium(VII) derivates can be prepared by the oxidation of cyclopentadienyltricarbonylrhenium compounds with hydrogen peroxide (*J. Organomet. Chem* 297, C5 (1985)). Overview articles on these rhenium compounds and their preparation are to be found in *Angew. Chem.* 100, 1269 (1988) and *J. Organomet. Chem.* 382, 1 (1990).

The organotrioxorhenium(VII) compounds III which are preferably used in the process of the invention are those in which $R^3$ is a $C_1$–$C_5$ alkyl group, a pentamethylcyclopentadienyl group or a phenyl group. It is particularly preferred to use methyltrioxorhenium(VII) and pentamethylcyclopentadienyltrioxorhenium(VII).

According to the invention, the rhenium catalysts III can be used in substance or in solution. In another embodiment of the process of the invention the rhenium compounds III are placed in the reaction zone in the form of deposits attached to a polymeric or mineral support. The polymeric supporting materials used for this purpose are preferably polymeric supporting materials carrying nitrogenous groups on their surface, such that the nitrogen atoms can be incorporated in both aromatic and aliphatic groups and also in amide or carbamate groups. As examples of such nitrogenous polymers there may be mentioned poly(vinyl pyrrolidone), poly(2-vinylpyridine), poly(2-vinylpyridine-co-styrene)s, polyacrylamides, polyimides, polyamides, and polyurethanes. These nitrogenous polymers fix the compounds III by a coordinate bond, so that these substances can be formulated as coordination compounds of formula VIII

(VIII)

in which the quotient b/a represents the ratio by weight of the two components and is generally from 0.01 to 0.2 and preferably from 0.02 to 0.1. The rule that generally applies is: as the rhenium content of VIII increases, the velocity of the isomerization reaction increases when using aliquot amounts of the catalyst VIII. The use of polymeric rhenium catalysts VIII of this kind has the advantage that the catalyst, on completion of the reaction, can be separated from the reaction mixture in an uncomplicated manner, e.g., by filtration. To effect preparation of polymeric catalysts VIII of this kind use is advantageously made of an impregnating process, in which the polymer concerned can be impregnated once or a number of times with a solution of the respective rhenium catalyst III in a suitable solvent e.g., an ether such as dimethoxyethane, tetrahydrofuran or dioxane, and then dried. For further details on the preparation of polymeric catalysts VIII cf DE-A 3,902,357.

Generally speaking, the catalysts of formula III are used in the process of the invention in amounts which are equivalent to a rhenium (calculated as Re) to α-alkenol molar ratio of from 1:50 to 1:5000 and preferably of from 1:75 to 1:2500 and more preferably from 1:100 to 1:1000. When use is made of polymer-attached rhenium catalysts of formula VIII, these are added to the allyl alcohol to be isomerized in such amounts that the rhenium (calculated as Re) to allyl alcohol molar ratio in the reaction mixture is generally from 1:50 to 1:5000 and preferably from 1:75 to 1:2500 and more preferably from 1:100 to 1:1000. The rhenium content of the polymer can be determined by radiofluorescence or atom emmision spectrometric methods.

The process of the invention can be carried out in the presence of air. Alternatively and preferably, it is carried out in an atmosphere of inert gas, e.g., under a blanket of nitrogen or argon.

Advantageously, the process of the invention is carried out at a temperature ranging from 0° to 300° C. and preferably from 10° to 200° C. and more preferably at from 20° to 150° C. As regards the reaction pressure the process of the invention is subject to no limitations and can be carried out under atmospheric pressure or an elevated or reduced pressure. Bearing in mind the subsequent working up of the reaction mixture, for example, in the case of continuous removal, by distillation, of an isomerization product from the reaction, it might be advantageous to use a pressure in the reaction equipment which is optimized for said distillation.

The process of the invention can be carried out in the presence or absence of solvents. It is an advantage to use solvents which are chemically stable under the reaction conditions and which do not impair the performance of the catalysts used. The solvents used are advantageously high-boiling solvents, e.g., ethers such as polyethylene glycol ether or polypropylene glycol ether, di- and tri-ethylene glycol dimethyl ethers, or high-boiling alkanols such as palmityl alcohol, stearyl alcohol, and cetyl alcohol, and also diethylene glycol and triethylene glycol, and high-boiling halogenated and preferably chlorinated hydrocarbons such as chlorobenzene, dichlorobenzene, and the like, carboxamides such as N,N-dimethylformamide, sulfoxides such as dimethylsulfoxide and sulfolan, or high-boiling hydrocarbons such as xylene, squalan, and paraffin oils. The amount of the solvent used is, as mention above, not usually of decisive importance and can be varied within wide limits. Generally speaking, the solvent is added in an amount of from 5 to 100 wt %, based on the weight of the reaction mixture without solvent.

Since the isomerization of the secondary to the primary α-alkenols and vice versa is, according to equation (3)

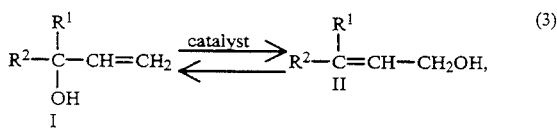

an equilibrium reaction, the isomerization reaction comes to a halt once a state of equilibrium has been reached, and there is obtained a product which is a mixture of the allyl alcohols I and II. If the allyl alcohol I is the desired product of the isomerization, it can be continuously distilled off from the reaction mixture at the same rate as it is formed, due to the fact that its boiling point is lower than that of compound II, and by this means the primary allyl alcohol II is quantitatively converted to the secondary allyl alcohol I.

If, on the other hand, the primary allyl alcohol I is the desired product of the isomerization, it is advantageously recovered by separating the reaction mixture, once a state of equilibrium has been reached, by distillation, into the allyl alcohols I and II, whilst the secondary allyl alcohol I is recycled to the reaction. In this embodiment of the process of the invention the use of a high-boiling solvent is advantageous. The catalyst remains in solution during distillation.

No limitations are known as concerns the use of the process of the invention for the isomerization of primary or secondary allyl alcohols of formula I or II, for example, the radical $R^1$ of these allyl alcohols can stand for a $C_1$-$C_{20}$ alkyl group and preferably a $C_1$-$C_{10}$ alkyl group and more preferably a $C_1$-$C_5$ alkyl group, or a $C_2$-$C_{20}$ alkenyl group and preferably a $C_2$-$C_{10}$ alkenyl group and more preferably a $C_2$-$C_8$ alkenyl group having one or two double bonds and preferably having one double bond. The radical $R^2$ of the allyl alcohols I and II can stand for, e.g., hydrogen or a $C_1$-$C_{20}$ alkyl group and preferably a $C_1$-$C_{10}$ alkyl group. In addition, $R^2$ can stand for a $C_1$-$C_{10}$ alkoxy group and preferably a $C_1$-$C_4$ alkoxy group, for a halogen atom, in particular a chlorine atom, or for a carbonyl group. Alternatively, the radicals $R^1$ and $R^2$ can be joined together to complete a five-membered or six-membered carbocyclic ring, which can contain one or two double bonds and preferably contains not more than one double bond, or is saturated. The radicals $R^1$ and/or $R^2$ can be unsubstituted or can carry from one to three substituents and preferably one substituent, which can be, e.g., a halogen atom, in particular a chlorine atom, a $C_1$-$C_4$ alkoxy group, a carbonyl group, or an oxo group.

The following α-alkenols may be given as examples of allyl alcohols which can be used in the process of the invention:

2-methyl-3-buten-2-ol, 1,7-octadien-3-ol, and linalool (3,7-dimethyl-1,6-octadien-3-ol), 1-vinyl-cyclohexanol, 1-hexen-3-ol, isophytol(3,7,11,15-tetramethyl-1-hexadecen-3-ol), and 2,3-dimethyl-3-buten-2-ol are examples of α-alkenols of formula I, and 1-buten-3-ol, 2-buten-1-ol (crotyl alcohol), 3-methyl-2-buten-1-ol (prenyl alcohol), 2,3-dimethyl-2-buten-1-ol, 2-hexen-1-ol, 2,7-octadien-1-ol, geraniol (3,7-dimethyl-2,6-octadien-1-ol), farnesol (3,7,11-trimethyl-2,6,10-dodecatrien-1-ol), phytol (3,7,11,15-tetramethyl-2-hexadecen-1-ol), vitamin A alcohol (retinol), 2-hexen-1-ol, and 2,3-dimethyl-2-buten-1-ol are examples of α-alkenols of formula II.

It is particularly preferred to use the process of the invention for the isomerization of 1,7-octadien-3-ol V to 2,7-octadien-1-ol IV and for the isomerization of but-1-en-3-ol VII to but-2-en-1-ol VI.

EXAMPLE

To 39.5 mg (0.16 mmol) of methyltrioxorhenium(-VII) in 40 g of xylene there were added dropwise, with stirring, at a temperature of 60° C., 3 g (23.8 mmol) of 1,7-octadien-3-ol in 10 mL of xylene. The reaction was carried out under a blanket of argon. Following a reaction time of 65 min, a state of equilibrium was reached which produced a conversion rate of 36%. The selectivity toward 2,7-octadien-1-ol was 100%.

We claim:

1. In a process for the catalytic isomerization of a secondary α-alkenol of the formula

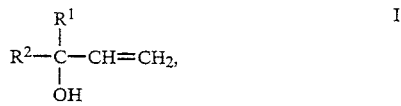

in which $R^1$ is a $C_1$-$C_{20}$-alkyl group or a $C_2$-$C_{20}$-alkenyl group and in which $R^2$ stands for hydrogen, halogen or a $C_1$-$C_{20}$-alkyl group and in which $R^1$ and $R^2$ can be joined together to complete a five-membered or six-membered carbocyclic ring, to form a primary α-alkenol of the formula

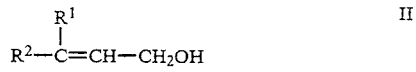

or for the isomerization of said primary α-alkenol of the formula II to said secondary α-alkenol of the formula I, the improvement which comprises:

carrying out the isomerization in the presence of a catalyst selected from the group consisting of organotrioxorhenium(VII) compounds of the formula

in which $R^3$ is a $C_1$-$C_{10}$-alkyl group, a cyclopentadienyl group substituted by from one to five $C_1$-$C_4$-alkyl groups, an unsubstituted cyclopentadienyl group, a $C_6$–$C_{10}$-aryl group, or a $C_7$–$C_{11}$-aralkyl group, and said organotrioxorhenium(VII) compounds of the formula III attached to a support.

2. A process as claimed in claim 1, wherein α-alkenols of formula I are produced by the isomerization of the α-alkenols of formula II while the α-alkenols of formula I are continuously distilled off from the isomerization mixture at the same rate as they are formed.

3. A process as claimed in claim 1, wherein α-alkenols of formula II are produced by the isomerization of the α-alkenols of formula I, while the isomerization mixture is separated in the presence of a high-boiling solvent and the α-alkenol of formula I is recycled to the reaction.

4. A process as claimed in claim 1, which is carried out at a temperature ranging from 0° to 300° C.

5. A process as claimed in claim 1, wherein said organotrioxorhenium(VII) compound III is attached by a coordinate bond to a nitrogeneous polymer support to form the coordinate compound of the formula

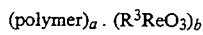
$(polymer)_a \cdot (R^3ReO_3)_b$   VIII wherein the ratio by weight a/b of the polymer to the compound III is from 0.01:1 to 0.2:1.

6. A process as claimed in claim 1, wherein the catalyst III is used in an amount which is equivalent to a molar ratio of rhenium/α-alkenol of from 1:50 to 1:5000.

7. A process as claimed in claim 5, wherein the catalyst III is used in an amount which is equivalent to a molar ratio of rhenium/α-alkenol of from 1:50 to 1:5000.

8. A process as claimed in claim 1, wherein the catalyst $R^3ReO_3$ III is selected from the group consisting of the compounds in which $R^3$ is a $C_1$–$C_5$-alkyl group, a pentamethylcyclopentadienyl group or a phenyl group.

9. A process as claimed in claim 1, wherein the catalyst $R^3ReO_3$ III is selected from the group consisting of methyltrioxorhenium(VII) and pentamethylcyclopentadienyltrioxorhenium(VII).

10. A process as claimed in claim 1, wherein the nitrogeneous polymer used as a support for the catalyst is selected from the group consisting of polyvinylpyrrolidone, poly(2-vinylpyridine), a copolymer of 2-vinylpyridine and styrene, polyacrylamides, polyimides, polyamides and polyurethanes.

11. A process as claimed in claim 1, wherein the process is carried out under a blanket of an inert gas.

* * * * *